US006231850B1

(12) United States Patent
Okano et al.

(10) Patent No.: US 6,231,850 B1
(45) Date of Patent: May 15, 2001

(54) CANINE INTERLEUKIN 12

(75) Inventors: Fumiyoshi Okano, Aichi; Masahiro Satoh, Kanagawa; Katsushige Yamada, Aichi, all of (JP)

(73) Assignee: Toray Industries, Inc. (JP)

( * ) Notice: Subject to any disclaimer, the term of this patent is extended or adjusted under 35 U.S.C. 154(b) by 0 days.

(21) Appl. No.: 09/079,984

(22) Filed: May 15, 1998

(30) Foreign Application Priority Data

May 16, 1997 (JP) .................................................. 9-127690

(51) Int. Cl.[7] .................................................. A61K 38/19
(52) U.S. Cl. .............................. 424/85.2; 514/2; 514/21; 530/350; 530/300; 530/339; 530/351; 435/335; 536/23.5
(58) Field of Search ......................... 424/85.2; 435/335; 514/21; 530/339, 351; 536/23.5

(56) References Cited

U.S. PATENT DOCUMENTS 5,573,764 * 11/1996 Sykes et al. ......................... 424/85.2

OTHER PUBLICATIONS

Belke–Louis (A), Cloning and sequence analysis of the p35 and p40 subunits of canine interleukin–12, GenBank Accession U49100, Mar. 13, 1996.*

Belke–Louis (B), Cloning and sequence analysis of the p35 and p40 subunits of canine interleukin–12, GenBank Accession U49085, Mar. 13, 1996.*

Ausubel et al, Current Protocols in Molecular Biology, Chapter 16, pp. 16.0.1–16.11.7, Jan. 1990.*

Paul et al Fundamental Immunology Third Edition. p. 826 Chapter 21, 1993.*

* cited by examiner

*Primary Examiner*—Julie Burke
(74) *Attorney, Agent, or Firm*—Austin R. Miller

(57) ABSTRACT

Canine interleukin 12 and a method for producing it by genetic engineering are disclosed. The canine interleukin 12 includes a protein having an amino acid sequence substantially the same as SEQ ID NO:1 or SEQ ID NO:11 or corresponds to part of either of SEQ ID NOS:1 and 11, and a protein having an amino acid sequence substantially the same as SEQ ID NO:2 or SEQ ID NO:12 or corresponds to part of either of SEQ ID NOS:2 and 12, and relates to a production method thereof. There is also an immune disease remedy and preventive agent for dogs and cats containing canine interleukin 12, and a method of treating immune disease and a preventive method for dogs and cats using the immune disease remedy or preventive agent.

15 Claims, No Drawings

CANINE INTERLEUKIN 12

TECHNICAL FIELD

An object of the present invention is to mass-produce canine interleukin 12 (hereinafter sometimes abbreviated "CaIL12") with the primary structure of its protein derived from canine genetic information for providing a drug for treatment of animals. Such drugs may be antitumor and antiviral in nature and can act as a vaccine adjuvant. The present invention relates to DNA sequences, recombinant vectors and transformants, CaIL12 itself and a production process thereof.

The present invention also relates to an immune disease remedy and preventive agent for dogs and cats comprising canine interleukin 12 with the primary structure of its protein derived from canine genetic information, and an immune disease treatment method and preventive method for dogs and cats using the remedy or preventive agent.

BACKGROUND ART

Interleukin 12 is a heterodimer consisting of a protein with a molecular weight of about 40 kD (hereinafter sometimes abbreviated "P40" or "P40 subunit") and a protein with a molecular weight of about 35 kD (hereinafter sometimes abbreviated "P35" or "P35 subunit"), and is a cytokine with such bioactivity as to activate natural killer cells and type 1 helper T cells, being abbreviated as IL12. Concerning IL12, some literature has been published. In addition to human IL12, the cDNAs of mouse IL12 (Shoenhaut et al: *J. Immunol.* 148, 3433–3440 (1992) and bovine IL12 (GenBank Database Registration Nos. U1 1815 and U14416) were cloned by gene manipulation techniques, and their application as remedies against cancers, viral diseases, etc. are being researched and developed.

For IL12, treatment effects in mouse model experiments against tumors, infectious diseases, allergies, and the like especially by its activity in boosting the cell-mediated immune response have been reported in the literature such as Nastala et al: *J. Immunol.* 153, 1697–1706 (1994), Gazzinelli et al: *Proc. Natl. Acad. Sci. USA* 90, 6115–6119 (1993) and Chirgwin et al: *Biochemistry* 18, 5294 (1979), and clinical trials of IL12 as a remedy against human cancer and human infectious disease has already started. However, it is not yet reported that canine IL12 has been cloned.

Dogs are known to suffer from various cancers such as mammary gland tumor, various viral diseases such as Parvovirus infectious disease and distemper infectious disease, allergic dermatitis and the like. Therefore, if canine IL12 were to become easily available, it is expected that its application as a canine antitumor drug, antiallergic drug and antiviral drug would be attempted.

Presently, few remedies and preventive agents effective against these canine diseases are available. For example, most dogs suffering from cancer come to hospitals after their tumors have grown, and even if the tumors are ablated by surgery, they soon die after the operation because of metastasis. Also, for skin diseases often seen with dogs, they cannot be cured in most cases even if steroids are administered repetitively for long periods of time as a treatment. As a consequence, fast and continuously acting remedies are being demanded. It is expected that new applications will be attempted for these canine diseases now left without any effective remedy if canine IL12 becomes available.

SUMMARY OF THE INVENTION

The invention includes cloning CaIL12 cDNA for mass-production and for providing a preparation containing CaIL12 as a remedy or preventive agent for dogs and cats suffering from immune diseases. The invention particularly includes cloning cDNAs coding for P40 and P35 of CaIL12 from canine cDNA and, furthermore, producing cells capable of producing CaIL12 using two expression plasmids linked to these cDNAs, respectively, and in producing recombinant Baculovirus containing both the genes.

Thus, the invention has established a method for mass-producing CaIL12 and found that if a preparation containing CaIL12 is administered to dogs and cats suffering from diseases difficult to treat by conventional therapeutic methods or if lymphocytes isolated from the peripheral blood of a sick dog or cat are stimulated in vitro by a preparation containing CaIL12 and returned into the body of the dog or cat again, the disease can be surprisingly remarkably improved.

The present invention provides plasmids capable of producing CaIL12, a transformant of *Escherichia coli* having these plasmids, animal cells transformed by these plasmids, CaIL12 obtained from these transformants, Baculovirus capable of producing CaIL12, CaIL12 produced by the Baculovirus, an immune disease remedy and preventive agent for dogs and cats containing CaIL12 as a main effective ingredient, and an immune disease treatment method and preventive method for dogs and cats. In addition, the present invention also provides cDNAs respectively coding for two subunits of CaIL12 protein.

Important aspects of the present invention include:

(1) Canine interleukin 12 comprises a P40 subunit and a P35 subunit and has at least one ability selected from 1) an ability to induce an antiviral active factor acting on canine leukocytes and a factor to intensify the expression of class II MHC of canine tumor cells, 2) an ability to promote the proliferation of canine lymphoblasts, and 3) an ability to damage canine tumor cells by activating canine leukocytes.

(2) Canine interleukin 12, stated in paragraph (1) above, wherein the P40 subunit has an amino acid sequence substantially the same as SEQ ID NO:1 or SEQ ID NO:11 or corresponding to part of either of those sequence.

(3) Canine interleukin 12, stated in paragraph (1) above, wherein the P35 subunit has an amino acid sequence substantially the same as SEQ ID NO:2 or SEQ ID NO:12 or corresponding to part of either of those sequences.

(4) An immune disease remedy and preventive agent for dogs and cats comprising canine interleukin 12 and a treatment method and preventive method using the remedy or preventive agent.

(5) A DNA sequence coding for the canine interleukin 12 stated in any one of paragraphs (1), (2) and (3) above, a recombinant vector containing it, a transformant obtained by transforming host cells by the recombinant vector, and a method of producing canine interleukin 12 by culturing the transformant or infecting insect cells or larvae with the transformant for culturing or raising.

BRIEF DESCRIPTION OF SEQUENCE LISTING

SEQ ID NO:1 sets forth the amino acid sequence for the P40 subunit of canine interleukin 12.

SEQ ID NO:2 sets forth the amino acid sequence for the P35 subunit of canine interleukin 12.

SEQ ID NO:3 sets forth the nucleotide sequence for one of the primers used in the cloning of CaIL12 P40 cDNA.

SEQ ID NO:4 sets forth the nucleotide sequence for one of the primers used in the cloning of CaIL12 P40 cDNA.

SEQ ID NO:5 sets forth the nucleotide sequence for one of the primers used in the cloning of CaIL12 P35 cDNA.

SEQ ID NO:6 sets forth the nucleotide sequence for one of the primers used in the cloning of CaIL12 P35 cDNA.

SEQ ID NO:7 sets forth the nucleotide sequence for a primer used in the preparation of a CaIL12 expression vector.

SEQ ID NO:8 sets forth the nucleotide sequence for a primer used in the preparation of a CaIL12 expression vector.

SEQ ID NO:9 sets forth the nucleotide sequence for a primer used in the preparation of a CaIL12 expression vector.

SEQ ID NO:10 sets forth the nucleotide sequence for a primer used in the preparation of a CaIL12 expression vector.

SEQ ID NO:11 sets forth the amino acid sequence for the P40 subunit of canine interleukin 12.

SEQ ID NO:12 sets forth the amino acid sequence for the P35 subunit of canine interleukin 12.

SEQ ID NO:13 sets forth the nucleotide sequence for a primer used in the preparation of a CaIL12 expression vector.

SEQ ID NO:14 sets forth the nucleotide sequence for a primer used in the preparation of a CaIL12 expression vector.

SEQ ID NO:15 sets forth the nucleotide sequence for a primer used in the preparation of a CaIL12 expression vector.

SEQ ID NO:16 sets forth the nucleotide sequence for a primer used in the preparation of a CaIL12 expression vector.

DETAILED DESCRIPTION OF THE INVENTION

Plasmids in which DNAs coding for the two subunits of CaIL12 protein of the present invention can be produced, for example, are described below. Two genes respectively coding for the two subunits showing CaIL12 activity can be cloned by polymerase chain reaction (hereafter sometimes abbreviated "PCR") of cDNAs synthesized after extracting poly(A)RNA from canine cells, using primers based on the gene sequences respectively coding for the two subunits of bovine or human IL12. As another method, the total length of CaIL12 P40 cDNA and CaIL12 P35 cDNA can be cloned by plaque hybridization of a phage library prepared from a synthesized cDNA recombinant, with two cDNA fragments obtained by PCR.

Usual methods can be used to obtain RNA from a canine organ or cells. For example, canine monocytes or lymphocytes stimulated by a mitogen or the like may be used. Such methods include isolating polysomes or using sucrose density gradient centrifugation or electrophoresis. RNA can be extracted from the canine organ or cells by any proper method selected from the guanidine thiocyanate cesium chloride method to effect CsCl density gradient centrifugation after guanidine thiocyanate treatment as disclosed by Nastala et al: *J. Immunol.* 153, 1697–1706 (1994), phenol extraction after treatment by a surfactant in the presence of ribonuclease inhibitor using a vanadium composite as disclosed by Gazzinelli et al: *Proc. Natl. Acad. Sci. USA* 90, 6115–6119 (1993), guanidine thiocyanate hot phenol method, guanidine thiocyanate guanidine hydrochloric acid method, guanidine thiocyanate phenol chloroform method, precipitation of RNA by treatment with lithium chloride after treatment with guanine thiocyanate and the like.

mRNA is isolated from a canine organ or canine monocytes or lymphocytes stimulated with a mitogen or the like by any ordinary method such as lithium chloride urea method, guanidine isocyanate method, or oligo dT cellulose column method, etc. A cDNA is synthesized from the obtained mRNA by any ordinary method such as Gubler et al.'s method or H. Okayama et al.'s method (Chirgwin et al: *Biochemistry* 18, 5294 (1979)). A reverse transcriptase such as avian myeloblastosis virus (AMV) is used to synthesize a cDNA from the obtained mRNA, as required in combination with DNA polymerase, etc. using a primer. However, it is convenient to use a marketed synthesizing or cloning kit.

cDNAs coding for the P40 subunit and P35 subunit showing CaIL12 activity can be cloned if PCR is effected with cDNAs as templates using a primer based on a human, mouse or bovine base sequence. As another method, synthesized cDNAs are linked with λ phage vectors, and mixed in vitro with a λ phage coated protein, etc., for packaging. *Escherichia coli*, acting as a host, are infected with the produced phage particles. In this case, the *Escherichia coli* infected with a λ phage are lysed and individual clones are collected as plaques. The plaques are transferred onto a filter of nitrocellulose or the like and by hybridization using the radio labeled genes obtained by PCR as a probe, the full length of CaIL12 P40 cDNA and CaIL12 P35 cDNA can be cloned.

A procaryote or eucaryote can be used as a host. The procaryotes which can be used here include bacteria, especially *Escherichia coli* or Bacillus such as *Bacillus subtilis*. The eucaryotes which can be used here include eucaryotic microbes such as yeasts, for example, Saccharomyces such as *Saccharomyces cerevisiae*, insect cells such as *Spodoptera frugiperda* cells, Trichoplusiani cells and *Bombyx mori* cells, and animal cells such as human cells, simian cells and mouse cells. In the present invention, organisms themselves, for examples, insects such as Trichoplusiani can also be used.

The expression vectors which can be used here include plasmids, phages, phagemids, viruses (Baculovirus), insects, vaccinia (animal cells) and the like. The promoter in the expression vector is selected depending on the host cells. For example, promoters for bacteria include lac promoter, trp promoter and the like, and promoters for yeasts include adhl promoter, pqk promoter and the like. Promoters for insects include Baculovirus polyhedrin promoter, p10 promoter and the like. Promoters for animal cells include early or late promoter of Simian Virus 40 and the like. However, the promoters which can be used are not limited to the above.

The transformation of a host by an expression vector can be effected by any conventional method well known to persons skilled in the art. These methods are stated, for example, in *Current Protocols in Molecular Biology*, John Wiley & Sons. Culturing transformants can also be effected according to conventional methods.

The produced CaIL12 has an apparent molecular weight of about 70 to 80 kD, if determined by sodium dodecylsulfate polyacrylamide gel electrophoresis (SDS-PAGE) under nonreducing conditions. The 70–80 kD band in SDS-PAGE produces two subunits of about 40 kD and about 35 kD in molecular weight under reducing conditions.

CaIL12 is mainly characterized by its ability to induce canine interferon γ from canine leukocytes and the effect of promoting the proliferation of canine lymphocytes stimulated with various mitogens such as phytohemagglutinin (hereinafter sometimes abbreviated as "PHA"). It also has activity to activate NK cells and cytotoxic T cells for killing their target cells, for example, the cell line derived from a tumor or fibroblasts infected with a virus.

The immune disease remedy and preventive agent for dogs and cats of the present invention shows a surprising remarkable treatment effect and preventive effect against various immune diseases of dogs and cats such as diseases declining in immunological competence such as tumors, dermatitis, allergic diseases and infectious diseases, and diseases showing partial immune reaction mainly relying on humoral reaction rather than on cellular immune reaction, compared to conventional remedies and preventive agents and treatment methods and preventive methods against these canine diseases.

The tumors of dogs and cats include mammary gland tumor, eosinophilic granuloma, epidermoid, ecphyma, lipoma, othematoma, pulmonary edema, dermal caulescent soft tumor, anal tumor and the like. Dermatitis of dogs and cats includes external acoustic meatus inflammation, dermatitis, eczema, dermatomycosis, pyoderma, allergic dermatitis, urtication, traumatic dermatitis and alopecia. Infectious diseases of dogs and cats include canine Parvovirus, distemper, feline AIDS, feline leukemia and the like. Allergic diseases include canine and feline pollinosis.

The immune remedy and preventive agent for dogs and cats can also contain other arbitrary ingredients in addition to CaIL12. The ingredients added to these medicines are mainly decided in reference to the medicine administration method. When the medicine is used as a solid, a filler such as lactose, binder such as carboxymethyl cellulose or gelatin, colorant and coating agent and the like can be used. Such a formulation is suitable for oral administration.

White Vaseline®, cellulose derivatives, surfactants, polyethylene glycol, silicone, olive oil and the like can be added as a solid or activator, to prepare a cream, emulsion, lotion and the like for application to the diseased part as an external medicine.

When the medicine is administered as a liquid, it can contain a physiologically permissible solvent, emulsifier and stabilizer as usually practiced. The solvent can be water or isotonic physiological salt solution such as PBS, and the emulsifier can be a polyoxyethylene based surfactant, fatty acid based surfactant, silicone or the like. The stabilizer can be canine serum albumin, a polyol such as gelatin or a saccharide such as sorbitol or trehalose. The method for administering the remedy and preventive agent of the present invention is not especially limited, but injection is expected to give the highest treatment affect. The methods of injection method are not limited. They include intravenous injection, intramuscular injection, hypodermic injection, intraperitoneal injection or intrapleural injection. The dosage is decided in reference to the size of the solid, administration method, disease concerned, symptom, etc., and an amount sufficient to manifest the treatment and/or preventive effect can be administered. For example, administration of CaIL12 by 0.1 pg to 100 μg/kg per day can provide a sufficient therapeutic effect.

In the case of adoptive immunotherapy, if 1 to 100 ml of lymphocytes isolated from canine blood are stimulated by 0.001 pg to 1 μg/kg of CaIL12 for 12 hours to 6 days and returned into the body again, a sufficient effect can be obtained.

EXAMPLES

The present invention is described below in reference to examples but is not limited thereto or thereby.

Example 1

Cloning of CaIL12 P40 and P35 genes:

(1) Preparation of canine cDNA

Total RNAs were extracted using ISOGEN (produced by Nippon Gene) from a canine liver, monocytes of the canine peripheral blood stimulated with LPS (50 μg/ml) for 48 hours and lymphocytes derived from a canine spleen treated by avian Newcastle disease virus for 7 hours ($10^7$ pfu/ml). Each of the obtained RNAs was dissolved into 10 mM Tris hydrochloric acid buffer (pH 7.5) containing 1 mM EDTA (hereinafter abbreviated as "TE"), and the solution was treated at 70° C. for 5 minutes. Then, the same amount of TE containing 1M LiCl was added. The RNA solution was applied to an oligo dT cellulose column equilibrated by TE containing 0.5M LiCl, and washed by the same buffer. Furthermore, it was washed by TE containing 0.3M LiCl, and poly(A)RNA adsorbed by 2 mM EDTA (pH 7.0) containing 0.01% SDS was eluted.

The poly(A)RNA thus obtained was used to synthesize a single stranded cDNA. That is, 5 μg of the poly(A)RNA and 0.5 μg of an oligo dT primer (12–18 mer) were supplied into a sterilized 0.5 ml microcentrifugation tube, and diethyl pyrocarbonate treated sterilized water was added, to make a total volume of 12 μl. The mixture was incubated at 70° C. for 10 minutes, and immersed in ice for 1 minute. To the mixture, 200 mM Tris hydrochloric acid (pH 8.4), 2 μl of 500 mM KCl solution, 2 μl of 25 mM $MgCl_2$, 1 μl of 10 mM each dNTP and 2 μl of 0.1 M DTT were added, and the mixture was incubated at 42° C. for 5 minutes.

Then, 1 μl of 200-unit SuperScript 11 RT produced by GibcoBRL was added, and the mixture was incubated at 42° C. for 50 minutes, for cDNA synthesizing reaction. The reaction mixture was further incubated at 70° C. for 15 minutes, and after the reaction was terminated, the reaction solution was placed on ice for 5 minutes. To the reaction solution, 1 μl of E. coli RNaseH (2 units/mi) was added, and the mixture was incubated at 37° C. for 20 minutes.

(2) Preparation of canine cDNA phage library

One microgram each of the poly(A)RNA obtained in paragraph (1) above was used to synthesize a double stranded cDNA using an oligo dT primer by Time Saver cDNA synthesizing kit produced by Pharmacia according to the manufacture's manual, and furthermore, EcoRI/NotI adaptor was linked. cDNA Rapid Cloning Module λgt10 produced by Amasham was used according to the manufacture's manual to produce recombinant λgt10 vector. In Vitro Packaging Module produced by Amersham was used according to the manufacture's manual to produce a recombinant phage.

(3) Cloning of CaIL12 P40 cDNA

The following two primers:

5'ATGTGTCACCAGCAGTTGGTCATCTCTTGGTTT 3'(SEQ ID NO:3), and

5'CTAACTGCAGGGCACAGATGCCCA3'(SEQ ID NO:4)

were synthesized by a DNA synthesizer based on the base sequences at the N-terminus and C-terminus of human IL12 P40, Wolf et al.: *J. Immunol.* 146, 3074–3081 (1991). The cDNAs obtained from a canine liver and the LPS stimulated canine peripheral blood in paragraph (1) above were taken by 2 μl each into different 0.5 ml micro centrifugation tubes, and respective reagents were added to contain 20 pmol of either of the primers, 20 mM Tris hydrochloric acid buffer (pH 8.0), 1.5 mM MgCl$_2$, 25 mM KCl, 100 μm/ml gelatin, 50 μM each dNTP and 4-unit TaqDNA polymerase, for achieving a total volume of 100 μl in each tube. The reaction was subjected to 35 amplification cycles on a DNA Thermal Cycler produced by Perkin-Elmer Cetus. The amplification cycle profile was 94° C. denaturation for 1 minute, 55° C. primer anneal for 2 minutes, and primer extension at 72° C. for 3 minutes. The PCR product was separated by electrophoresis in a 1% agarose gel, and an about 990 bp DNA fragment was prepared according to a conventional method disclosed by Berger et al.: *Biochemistry* 18, 5143 (1979).

The DNA fragment was linked to T-Vector produced by Invitrogen using DNA Ligation Kit Ver. 1 produced by Takara Shuzo Co., Ltd. *E. coli* was transformed according to a conventional method. A plasmid DNA was prepared from the obtained transformant according to a conventional method. It was confirmed by PCR under the same conditions as mentioned before that the plasmid had a PCR fragment inserted, and the base sequence of the P40 subunit cDNA of the two subunits considered to show CaIL12 activity by the dideoxy method as disclosed by Okayama et al.: *Mol. Cell. Biol.*, 2, 161 (1982) and 3, 280 (1983) was determined using Genesis 2000 DNA analysis system (produced by DuPont). The sequence is shown as SEQ ID NO:1.

A 990 bp DNA fragment containing this sequence was labeled with $^{32}$pdcTP using Random Primer DNA Labeling Kit produced by Takara Shuzo Co., Ltd. to prepare a probe. The recombinant phage library prepared from the canine liver cDNA obtained in paragraph (2) above was formed as a plaque on *E. coli* NM514, and transferred onto Hybond-N +produced by Amersham according to a conventional method. The Hybond-N+was incubated in 5×SSPE (0.9 M NaCl, 50 mM NaH$_2$PO$_4$, 5 mM EDTA, pH 7.4), 5×Denhardt's solution (0.1% Ficoll, 0.1% polyvinylpyrrolidone, 0.1% bovine serum albumin), 0.1% SDS, 100 μg/ml salmon sperm DNA at 65° C. for 2 hours, and hybridized with 1×10$^6$ cpm/ml of the labeled probe prepared as described above. After overnight incubation at 65° C., the Hybond-N + was washed in 0.2×SSC (30 mM NaCl, 3 mM sodium citrate), 0.1% SDS for 15 minutes three times, and exposed to Fuji Imaging Plate produced by Fuji Photo Film Co., Ltd. for 12 hours, being analyzed by Bioimaging Analyzer produced by Fuji Photo Film Co., Ltd.

The plaques with a positive signal were re-screened according to a conventional method. One recombinant phage with a positive signal was obtained as a result of screening three times. From the recombinant phage, a phage DNA was extracted according to a conventional method and cleaved by the restriction enzyme EcoRi. A DNA fragment was obtained by 1% agarose gel electrophoresis and linked to pUC118BAP treated DNA (EcoRI/BAP) produced by Takara Shuzo Co., Ltd. using DNA Ligation Kit Ver. 2 produced by Takara Shuzo Co., Ltd. A plasmid DNA was prepared according to a conventional method and the base sequence of the obtained DNA fragment was determined using a fluorescent DNA sequencer (DNA Sequencer 373S produced by Perkin-Elmer) and Dye Terminator Cycle Sequencing Kit produced by Perkin-Elmer according to the manufacture's manual. Of that sequence, the sequence coding for CaIL12 P40 cDNA is shown as SEQ ID NO:11.

(4) Cloning of CaIL12 P35 cDNA

The following two primers:

5'AGCATGTGTCCAGCGCGCAGCCTCCTCCTTG TCGCTACCCTG3'(SEQ ID NO:5) and

5'CTAGGAAGAACTCAGATAGCTCATCATTCTGT CGATGGT3'(SEQ ID NO:6)

were synthesized by a DNA synthesizer based on the base sequences at the N-terminus of human IL12 P35 as disclosed by Wolf et al.: *J. Immunol.* 146, 3074–3081 (1991) and the C-terminus of bovine IL12 P35. An about 670 bp DNA fragment was obtained as described in paragraph (3) above, using the cDNA obtained from lymphocytes derived from a canine spleen treated by avian Newcastle disease virus of paragraph (1) above as a template, and inserted into the T-Vector. The base sequence of the P35 subunit cDNA out of the two subunits considered to show CaIL12 activity was determined. The sequence is shown as SEQ ID NO:2.

An about 670 bp DNA fragment containing this sequence was used to prepare a radio labeled probe. The recombinant phage library prepared from the cDNA obtained from lymphocytes derived from a canine spleen treated by avian Newcastle disease virus obtained in paragraph (2) above was hybridized with the labeled probe as described in paragraph (3) above, and the hybrid was screened. A DNA was extracted and cleaved by the restriction enzyme NotI from one recombinant phage with a positive signal obtained as a result, separated by 1% agarose gel electrophoresis, and an about 1.2 kb DNA fragment was obtained. It was linked to the NotI site of pBluescript 11 produced by Stratagene according to a conventional method. It was used to prepare a plasmid DNA, and the base sequence of the obtained DNA fragment was determined using a fluorescent DNA sequencer. Of that sequence, the sequence coding for CaIL12 P35 cDNA is shown as SEQ ID NO:12.

Example 2

Production of CaIL12:

(1) Preparation of CaIL12 expression vector

Expression vector pCDL-SRα296 as described in Okayama et al.: *Mol. Cell. Biol.*, 2, 161 (1982) and *Mol. Cell Biol.* 3, 280 (1983) was cleaved with the restriction enzyme EcoRI, and the terminus was dephosphorylated by an alkaline phosphatase derived from a bacterium. An about 3.6 kb DNA fragment was prepared according to a conventional method with 1% agarose gel electrophoresis. On the other hand, as the CaIL12 P40 cDNA fragment, an about 990 bp DNA fragment was prepared by preparing the following two primers with the EcoRI cleaved region added:

5'GGGGAATTCATGTGTCACCAGCAGTTGGTCAT CTCTTGG3'(SEQ ID NO:7) and

5'CCCGAATTCCTAACTGCAGGGCACAGATGCCC AGTCGCT3'(SEQ ID NO:8).

Using these primers, DNA was amplified by 30 cycles of PCR using the P40 subunit DNA out of the two subunits considered to show CaIL12 activity inserted in the T-Vector prepared in Example 1 (2) as a template. The PCR profile was denaturation of the DNA at 94° C. for 1 minute, annealing the primer at 55° C. for 2 minutes and elongating the primer at 72° C. for 3 minutes. The amplified DNA was ethanol precipitated, cleaved by the restriction enzyme EcoRI, and separated using 1% agarose gel electrophoresis.

An about 990 bp DNA fragment was prepared by preparing the following two primers with the EcoRI cleaved region added:

5'GGGGAATTCATGCATCCTCAGCAGTTGGTCAT CTCCTGG3'(SEQ ID NO:13) and

5 'CCCGAATTCCTAACTGCAGGACACAGATG CCCAGTCGCT3'(SEQ ID NO:14).

Using these primers, DNA was amplified by PCR using the CaIL12 P40 cDNA inserted in pUC 118 prepared in Example 1 (2) as a template, and cleaving by EcoRi. The obtained respective CaIL12 P40 cDNA fragments were linked to the pCDL-SRα296 prepared as described above, using T4DNA ligase. This was used to transform *E. coli*. A plasmid DNA was prepared from the obtained transformant to obtain FO CaIL12 P40 and FO CaIL12 P40FL expressing CaIL12 P40.

pCDL-SRα296 was cleaved by the restriction enzyme PstI, and dephosphorylated. Electrophoresis was effected to prepare an about 3.5 kb DNA fragment. As the CaIL12 P35 DNA fragment, an about 670 bp DNA fragment was obtained by preparing the following two primers with the PstI cleaved region added:

5'GGGCTGCAGATGTGTCCAGCGCGCAGCCTCCT CCTTGTC3'(SEQ ID NO:9) and
5'GGGCTGCAGCTAGGAAGAACTCAGATAGCTCA TCATTCT3'(SEQ ID NO:10).

Using these primers, the DNA was amplified by 30 cycles of PCR using the P35 subunit DNA out of the two subunits considered to show CaIL12 activity inserted in the T-Vector prepared in Example 1 (3) as a template, at 94° C. for 1 minute, at 55° C. for 2 minutes and at 72° C. for 3 minutes. The amplified DNA was ethanol precipitated, cleaving by restriction enzyme PstI, and separated by 1% agarose gel electrophoresis.

An about 670 bp DNA fragment was prepared by preparing the following two primers with the PstI cleaved region added:

5'GGGCTGCAGATGTGCCCGCCGCGCGGCCTCCT CCTTGTG3'(SEQ ID NO:15) and
5'GGGCTGCAGTTAGGAAGAATTCAGATAACTCA TCATTCT3'(SEQ ID NO:16).

Using these primers, the DNA was amplified by PCR using the CaIL12 P35 DNA inserted in pUCI 18 prepared in Example 1 (2) as a template, and cleaving by PstI. The obtained respective CaIL12 P35 DNA fragments were linked to PstI-cleaved pCDL-SRα296 using T4 DNA ligase, which was to be used for transforming *E. Coli* and preparing a plasmid DNA as described above, to obtain FO CaIL12 P35 and FO CaIL12 P35 FL expressing CaIL12 P35.

The base sequences of CaIL12 P40 DNA and CaIL12 P35 DNA in these four expression plasmids prepared were confirmed.

(2) Production of CAIL12 by COS-1 cells

Five micrograms each of the FO CaIL12 P40 and FO CaIL12 P35 obtained in the paragraph (1) above were added to 4 ml an ERDF medium (produced by Kyokuto Seiyaku K. K.) containing 50 mM Tris hydrochloric acid buffer (pH 7.5), 400 μg/ml DEAE dextran (produced by Pharmacia) and 100 μM of chloroquine (produced by Sigma). On the other hand, the COS-1 cells (ATCC CRL-1650) grown until 50% confluent in an ERDF medium containing 10% fetal bovine serum (produced by Gibco, hereinafter abbreviated as FBS) using a 10 cm dia. dish were washed by PBS once, and 4 ml of the DNA mixture obtained in the above was added. The mixture was cultured in 5% $CO_2$ at 37° C. Four hours later, the cells were washed by PBS, and cultured in 10 ml of 10% FBS-ERDF medium in 5% $CO_2$ at 37° C. for 4 days, to obtain a cultured supernatant containing produced CaIL12.

(3) Preparation of recombinant Baculovirus capable of producing CaIL12

To the restriction enzyme XbaI and SmaI cleaved regions downstream of the promoter of Baculovirus transfer vector pAcAB3 (produced by Pharmingen), p40 and p35 subunit cDNAs were linked respectively according to a conventional method, to obtain a recombinant transfer vector. Furthermore, recombinant Baculovirus was prepared using Baculovirus Transfection Kit produced by Pharmingen according to the attached manual.

(4) Production of CaIL12 by insect cells

The recombinant Baculovirus obtained in paragraph (3) above was infected into Sf21 cells (derived from *Spodoptera frugiperda*, obtained from Pharmingen) plate-cultured until confluent in a 75 cm² flask in Baculo Gold Protein-Free Insect Medium produced by Pharmingen, and the infected cells were cultured for 4 days, to obtain a cultured supernatant containing produced CaIL12.

(5) Activity measurement of CaIL12

The activities of the CaIL12 produced in paragraphs (2) and (4) above were measured as described below. To test the activity to induce canine interferon γ from canine lymphocytes, the antiviral activity and the activity to intensity the class 11 MHC expression of canine cells were measured.

From a canine spleen, lymphocytes were isolated and suspended in 10% FBS-ERDF at a cell density of $10^6$ cells/ml. 2.5 ml was added to a 6 cm dish, and 2.5 ml of the cultured supernatant obtained in paragraph (2) above was added. The mixture was cultured in 5% $CO_2$ at 37° C. for 2 days, and the antiviral activity of the cultured supernatant was measured according to the CPE method of Molecular Cloning, Cold Spring Harbor Laboratory, New York (1982) using Vesicular Stomatitis Virus as a virus and MDCK (ATCC CCL-34) as sensitive cells. As a result, an antiviral activity of more than $10^5$ dilution units/ml was confirmed. On the other hand, a cell culture supernatant obtained as a control by introducing 10 μg of pCDL-SRα296 into COS-1 cells as in paragraph (2) above did not show any ability to induce the antiviral activity.

Cell strain FCBR1 derived from canine mammary gland tumor tissue expressing class II MHC was used to measure the class II MHC expression intensifying activity of said cultured supernatant of canine spleen lymphocytes. To a 6 cm dish, $10^5$ cells of FCBR1 were attached, and 5 ml of the cultured supernatant of canine spleen lymphocytes stimulated by CaIL12 was added to it, for culturing in 5% $CO_2$ at 37° C. overnight. After completion of culturing, the cells were detached by trypsin, and centrifuged by a 1.5 ml micro centrifugation tube. 10 μl of rat anti-canine MHC class II monoclonal antibody (produced by Stratagene) was added and the mixture was suspended in 50 μl of 10% FBS-ERDF.

The suspension was incubated on ice for 1 hour. It was washed by PBS and suspended in 5 μl of FITC labeled rabbit anti-rat monoclonal antibody (produced by Stratagene) and 50 μl of 10% FBS-ERDF, and the suspension was incubated on ice for 1 hour. It was washed with PBS and analyzed by FACScan produced by Becton Dickinson K. K. As a result, the cultured supernatant of canine spleen lymphocytes stimulated by CaIL12 increased the expression of class II MHC on FCBR1 by about 20%. From this, it was found that CaIL12 has activity to act on canine lymphocytes for inducing canine interferon γ.

The activity to promote the proliferation of canine lymphoblasts was measured. From canine peripheral blood, lymphocytes were isolated and suspended by 10% FBS-ERDF at a cell density of $10^6$ cells/ml, and of them, 5 ml was added to a 6 cm dish. PHA (produced by ICN) was added at a concentration of 5 μg/ml, and the mixture was cultured in 5% $CO_2$ at 37° C. for 3 days, to make the lymphocytes blastogenic. The lymphoblasts were suspended in 10% FBS-ERDF at a cell density of $10^6$ cells/ml, and 50 μl of the suspension was added per well of a 96-well microplate. The cultured supernatant obtained in paragraph (2) above was added by 50 μl per well. As a control, 10% FBS-ERDF was added by 50 μl per well. They were cultured in 5% $CO_2$ at 37° C. for 3 days, and the activity of CaIL12 to promote the proliferation of lymphoblasts was measured according to the MTT assay method of Prober et al.: *Science* 238, 336–341 (1987).

5 mg/ml of MTT (produced by Sigma) solution was added by 10 μl per well, and the mixture was cultured for 6 hours.

One hundred and fifty microliters of 0.04N isopropanol hydrochloride solution was added and the cells were crushed ultrasonically. The absorbance at a wavelength of 595 nm was measured by a microplate reader (Model 13550 produced by BIO-RAD). The average absorbance of the control was 0.69, while the average absorbance of CaIL12 was 1.52, showing that the activity to promote the proliferation of lymphoblasts was about twice as high.

The antitumor effect of CaIL12 against canine tumors was examined. Lymphocytes were isolated from canine peripheral blood and suspended in 10% FBS-ERDF at a cell density of $5 \times 10^6$ cells/ml, and of them, 5 ml was added to a 6 cm dish. 500 U of recombinant human IL2 produced by Beringer-Manheim K. K. was added and the mixture cultured in 5% $CO_2$ at 37° C. for 3 days. On the other hand, canine tumor cell lines FCBR1 and A72 (ATCC CRL-1542) were suspended in 10% FBS-ERDF at a cell density of $10^5$ cells/ml, respectively, and the suspensions were respectively added to a 96-well plate by 50 μper well for adhesion to the plate. 50 μl of canine lymphocytes stimulated by human IL2 were added and 100 μl of the cultured supernatant expressing CaIL12 obtained in paragraph (2) above or 100 μl of 10% FBS-ERDF as a control was added. The mixture was cultured in 5% $CO_2$ at 37° C. for 2 days. The supernatant was removed completely after completion of culturing, and an MTT assay was performed. Cytotoxicity % was calculated from the following formula:

$$\text{Cytotoxicity \%} = (1-OD_2/OD_1) \times 100$$

where $OD_1$ is the absorbance of canine tumor cells cultured in a medium only at a wavelength of 595 nm, and $OD_2$ is the absorbance of canine tumor cells cultured with canine lymphocytes at a wavelength of 595 nm.

As a result, in the case of FCBR1, while the control showed a cytotoxicity of 34%, CaIL12 showed a cytotoxicity of 75%. In the case of A72, while the control showed 22%, CaIL12 showed 83%. From these, it was found that CaIL12 activates canine lymphocytes to express antitumor effect against canine tumor cells.

Example 3
Purification of CaILI2:

Two hundred and fifty milliliters of the cell cultured supernatant obtained in Example 2 (4) was applied to a column packed with a sulfopropyl carrier, and the column was washed by a sufficient quantity of 20 mM phosphoric acid buffer. Adsorbed fractions were obtained by elution with 0.5–1M NaCl, applied to a Blue Sepharose carrier, and washed similarly, and elution was effected with 1.1–2M NaCl, to obtain fractions. The obtained fractions were desalted by dialysis, to obtain 5 ml of a purified CaIL12 fraction. The purity of CaIL12 in the fraction was more than 90% according to SDS-PAGE analysis.

Example 4
Production of CaIL12 preparation:

Physiological salt solution for injection, low molecular gelatin for injection (produced by Nitta Gelatin K. K.) and sorbitol were added to the purified CaIL12 solution obtained in Example 3 to achieve a final gelatin concentration of 0.5% and a final sorbitol concentration of 30%. The mixture was treated by Posidyne (produced by Pall K. K.) to remove the pyrogen and the residue was dispensed with 1 ml each into glass vials sterilized in dry heat at 250° C. for 2 hours. Subsequently, the sterile solution was freeze-dried to obtain a CaIL12 preparation as vials containing 1 pg to 5 μg of CaIL12 each. The CaIL12 preparation was stable at room temperature and dissolved well into distilled water or physiological salt solution.

Example 5
Evaluation of medicinal effect of CaIL12 preparation at cell level:

(1) Tumors

To see the antitumor effect of the CaIL12 preparation, tumor-bearing mice were produced, and canine lymphocytes stimulated by the CaIL12 preparation were injected to examine the tumor reducing effect. Ten 6-week-old female nude mice (BALB/C nu/nu) were purchased from Nippon Crea K. K. Canine mammary gland tumor cell line FCBR1 ($10^8$ cells) was transplanted subcutaneously in the back of each mouse. About one month later, tumor-bearing mice with a tumor of 33 mm ×25 mm on the average were produced. On the other hand, when FCBR1 was established, $10^8$ cells of tumor infiltrating lymphocytes (hereinafter abbreviated as "TILs") isolated according to the method as disclosed by Whiteside et al.: *J. Immunol. Methods* 90, 221–223 (1986) were suspended in 20 ml of 10% FBS-ERDF, and 10 ng of the CaIL12 preparation prepared in Example 4 was added. The mixture was cultured in 5% $CO_2$ at 370C. for 2 days, to obtain TILs stimulated by CaIL12 preparation.

As a control, $10^8$ cells of TILs cultured under similar conditions without adding the CaIL12 preparation were obtained. These two TIL samples were injected into the tumor-bearing nude mice intravenously, five mice each, with $10^7$ cells per mouse. The weight of each tumor was measured by vernier calipers seven days after injection, to examine the difference from the tumor weight measured before injecting each TIL. The weight of each tumor was calculated from the following formula:

$$\text{Weight of a tumor} = (\text{length} \times \text{width}^2/2)$$

Out of five tumor-bearing mice into which the TILs stimulated by the CaIL12 preparation were injected, three mice showed perfect regression of the tumor and two mice were less than 0.2 in the relative tumor weight with the tumor weight before TIL injection as 1. On the other hand, in all five tumor-bearing mice into which the control TILs were injected increased in tumor weight, and all the relative tumor weights were more than 1.25. From the results, it was found that the CaIL12 preparation activated the TILS, expressing the tumor reducing effect.

2) Allergy

To see the anti-allergic effect of the CaIL12 preparation, lymphocytes derived from dogs suffering from an allergic disease were stimulated by CaIL12 preparation to examine whether the preparation could control the expression of allergy causing factors such as IgE. From five dogs diagnosed to suffer from atopic dermatitis, 10 ml each of blood was sampled. From the respective samples, lymphocytes were immediately isolated and to each of the lymphocyte samples, 10 ng of the CaIL12 preparation was added in 10% FBS-ERDF in a 10 cm dish immobilized with anti-human CD3 polyclonal antibody (produced by Genzyme), for culturing for 3 days.

As a control, canine lymphocytes cultured under similar conditions without adding the CaIL12 preparation were prepared. After completion of culturing, some lymphocytes were collected from each dish, and a cDNA was synthesized as described in Example 1. PCR was performed using primers specific to canine IgE and canine IgE receptor cDNAs to examine the expression of the cDNAs. As a result, the expression of the cDNAs in the canine lymphocytes cultured with the CaIL12 preparation was found to be inhibited with every sample compared to the expression achieved without adding the CaIL12. From the results, it was found that the CaIL12 preparation acts on canine lymphocytes to inhibit the expression of IgE and IgE receptor which are allergy causing factors.

According to the panning method, disclosed by Seed et al.: *Proc. Natl. Acad. Sci. USA*84, 3365–3369 (1986), using anti-human CD4 polyclonal antibody (produced by Genzyme), from the lymphocytes remaining in each dish, CD4 positive cells mainly formed by a helper T cell population were obtained. They were used to synthesize a cDNA, and PCR was performed using primers specific to CaIL5 and CaIFN γgenes to examine the expression of the cDNAs. As a result, it was found that the expression of CaIL5 cDNA was inhibited by the addition of the CaIL12 preparation in every case. On the other hand, the expression of CaIFN γcDNA was intensified by the addition of the CaIL12 preparation in every case.

IL5 is produced from type 2 helper T cells causing humoral immune reaction such as allergic reaction. On the other hand, IFN γis produced from type 1 helper T cells which cause cellular immunity and inhibit humoral immunity. From the results, it was suggested that the CaIL12 preparation inhibits the type 2 helper T cells in canine lymphocytes and activate type 1 helper T cells. From these results, it was found that the CaIL12 preparation is promising for treating the allergic diseases of dogs.

Example 6

Toxicity test of CaIL12 preparation for dogs:

The toxicity of the CaIL12 preparation was tested according to the following procedure. Three beagles were used as test animals.

(1) Administration method

The preparation was administered every other day 5 times in total. The dosage was gradually increased (1 ng/kg body weight the 1st time, 5 ng/kg body weight, 25 ng/kg body weight, 250 ng/kg body weight and 1 µg/kg body weight the 5th time). The preparation was administered intravenously.

(2) Observation period, observation items and observation time points

The observation period was from one week before the start of administration until three weeks after start of administration. The observation items included clinical symptoms (respiratory pattern, vitality, appetite, activity, visible mucous membranes, saliva, evacuation action, somnolence), body temperature, heart rate, body weight, hematological examination (hemocytometry leukocyte count, hematocrit, thrombocyte count, hemogram), electrolyte (Na, K, Cl), biochemical examination (BUN, Crea., GOT, GPT, CPK, Glucose, TP, Alb, Glob, A/G), urine finding, circulatory organs and automatic nervous system finding. Body weight was measured every 7 days after the date of administration, and the other items were measured one week before the start of administration, immediately before the date of administration, 10 minutes after, 30 minutes after, 1 hour after, 1.5 hours after, 2 hours after, 4 hours after, 6 hours after, 12 hours after, 24 hours after, 48 hours after, 2 weeks after the start of administration and 3 weeks after the start of administration.

As a result of testing according to the above procedure, the administration of the CaIL12 preparation did not show any change to be taken up as a problem. It has been shown that the CaIL12 preparation is not toxic to dogs at least up to the largest dosage of 1 µg/kg body weight.

Example 7

Treatment and prevention of dog diseases by CaIL12 preparation:

Twelve dogs with tumors on the epidermis were injected with the CaIL12 preparation locally and intravenously. Every dog had a plurality of differently sized tumors. Of the twelve dogs, eight dogs were injected with the CaIL12 by 10 ng–1 µg per tumor locally at the tumors every 3 to 4 days 3 to 10 times in total. As a result, 90% of the tumors injected with the CaIL12 completely vanished, and all the remaining tumors were reduced to less than a half each. Four dogs had tumors of more than 100 cm$^3$ and had them metastasized to viscera such as lungs, livers and kidneys. Of the three dogs, the tumors on the epidermis were ablated by surgical operation and, immediately, the dogs were intravenously injected with the CaIL12 preparation by 10 ng/kg. Subsequently, they were injected every day for 7 days at a dosage uf 500 ng/kg. As a result, all of the tumors metastasized that had to the viscera vanished, and recurrence was not observed at all for six months.

Seven dogs diagnosed as suffering from atopic dermatitis were intravenously injected with the CaIL12 preparation. These dogs were observed to have clinical symptoms such as erythema, eczema, alopecia, etc. on the skin, and much IgE was detected in the blood. In their leukocyte fractions, respective mRNAs of IL4, IL5, IL10 and IL13 were highly expressed. The dogs were intravenously injected with the CaIL12 preparation at doses of 0.1 to 100 ng/kg every 3 days 3 to 5 times in total. The clinical symptoms quickly improved after one injection and were cured after 3 to 5 injections.

Three dogs diagnosed as suffering from pollinosis were intravenously injected with the CaIL12 preparation. By administering one dose at a dosage of 0.1 to 10 pg/kg, such clinical symptoms as sneezing and sniveling were quickly improved.

Example 8

Treatment of canine diseases by adoptive immunotherapy using the CaIL12 preparation:

25 ml of blood was sampled from each of five dogs and two cats diagnosed to have tumors on the epidermis and three dogs diagnosed to suffer from atopic dermatitis. Lymphocytes were isolated from each of the samples, and 50 U of human IL2 (produced by Genzyme) and 100 ng of the CaIL12 preparation were added in 10% FBS-ERDF in a 10 cm dish immobilizied with anti-human CD3 polyclonal antibody (produced by Genzyme). The mixtures were cultured for 4 days. Lymphocytes were collected after completion of culturing and intravenously injected into the respective dogs and cats. As a result, all the three dogs suffering from atopic dermatitis were cured, and the dogs and cats with tumors showed a tendency of tumor reduction. The same operation was repeated every week 3 to 5 times in total, and all the tumors regressed.

INDUSTRIAL APPLICABILITY

The present invention can provide a remedy, treatment method, preventive and preventive method excellent against tumors, dermatitis, infectious diseases and allergic diseases of dogs and cats.

What is claimed is:

1. Isolated canine interleukin 12 comprising a P40 subunit and a P35 subunit having at least one activity selected from the group consisting of an activity to induce an antiviral active factor acting on canine leukocytes and a factor to intensify expression of class II MHC of canine tumor cells, an activity to promote proliferation of canine lymphoblasts, and an activity to kill canine tumor cells by activating canine leukocytes, wherein said P40 subunit comprises an amino acid sequence encoded by a polynucleotide selected from the group consisting of SEQ ID NO:1, and SEQ ID NO:11.

2. Canine interleukin 12 according to claim 1, wherein said P35 subunit comprises an amino acid sequence encoded by a polynucleotide selected from the group consisting of SEQ ID NO:2, and SEQ ID NO: 12.

3. Isolated canine interleukin 12 comprising a P40 subunit and a P35 subunit and having at least one activity selected from the group consisting of an activity to induce an antiviral active factor acting on canine leukocytes and a factor to intensify expression of class II MHC of canine tumor cells, an activity to promote proliferation of canine lymphoblasts, and an activity to kill canine tumor cells by activating canine leukocytes, wherein said P35 subunit comprises an amino acid sequence encoded by a polynucleotide selected from the group consisting of SEQ ID NO:2 and SEQ ID NO:12.

4. A pharmaceutical composition as an immune disease remedy for dogs or cats comprising a therapeutically effective amount of the isolated canine interleukin 12 stated in claims 1 or 3 wherein said immune disease is selected from the group consisting of allergy tumors and dermatitis.

5. A pharmaceutical composition as an immune disease preventive agent for dogs or cats comprising an immune disease preventative amount of the isolated canine interleukin 12 as defined in claims 1 or 3 wherein said immune disease is selected from the group consisting of allergy, tumors, disease and dermatitis.

6. The composition according to claim 4, wherein said effective amount of said isolated canine interleukin 12 is about 0.1 pg/kg to about 100 µg/kg based on body weight.

7. The composition according to claim 6, wherein said remedy is provided in an injectable form.

8. The composition according to claim 5, wherein said effective amount of said isolated canine interleukin 12 is about 0.1 pg/kg to about 100 µg/kg based on body weight.

9. The composition according to claim 8, wherein said immune disease preventative agent is provided in an injectable form.

10. The composition according to claim 4, wherein said remedy is provided as a liquid dosage form.

11. The composition according to claim 4, wherein said remedy is provided in a dosage cream.

12. The composition according to claim 4, wherein said remedy is provided as a solid dosage form.

13. The composition according to claim 5, wherein said immune disease preventative agent is provided in a liquid dosage form.

14. The composition according to claim 5, wherein said immune disease preventative agent is provided in a dosage cream.

15. The composition according to claim 5, wherein said immune disease preventative agent is provided in a solid dosage form.

* * * * *

UNITED STATES PATENT AND TRADEMARK OFFICE
CERTIFICATE OF CORRECTION

PATENT NO. : 6,231,850 B1
DATED : May 15, 2001
INVENTOR(S) : Okano et al.

It is certified that error appears in the above-identified patent and that said Letters Patent is hereby corrected as shown below:

<u>Column 30,</u>
Line 4, please delete "disease" after -- tumors, --.

Signed and Sealed this

Sixteenth Day of April, 2002

Attest:

Attesting Officer

JAMES E. ROGAN
*Director of the United States Patent and Trademark Office*

SEQUENCE LISTING (1) GENERAL INFORMATION:

(iii) NUMBER OF SEQUENCES: 16

(2) INFORMATION FOR SEQ ID NO: 1:

(i) SEQUENCE CHARACTERISTICS:
        (A) LENGTH: 990 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: Canis familiaris (ix) FEATURE:
        (A) NAME/KEY: Canine IL12
        (B) LOCATION: 1 to 987
        (C) IDENTIFICATION METHOD: Similarity (xi) SEQUENCE DESCRIPTION: SEQ ID NO: 1:

```
ATG TGT CAC CAG CAG TTG GTC ATC TCT TGG TTT TCC CTC GTT TTG CTG        48
Met Cys His Gln Gln Leu Val Ile Ser Trp Phe Ser Leu Val Leu Leu
1               5                   10                  15

GCG TCT CCC CTC ATG GCC ATA TGG GAA CTG GAG AAA GAT GTT TAT GTT        96
Ala Ser Pro Leu Met Ala Ile Trp Glu Leu Glu Lys Asp Val Tyr Val
            20                  25                  30

GTA GAG TTG GAC TGG CAC CCT GAT GCC CCC GGA GAA ATG GTG GTC CTC       144
Val Glu Leu Asp Trp His Pro Asp Ala Pro Gly Glu Met Val Val Leu
        35                  40                  45

ACC TGC CAT ACC CCT GAA GAA GAT GAC ATC ACT TGG ACC TCA GCG CAG       192
Thr Cys His Thr Pro Glu Glu Asp Asp Ile Thr Trp Thr Ser Ala Gln
    50                  55                  60

AGC AGT GAA GTC CTA GGT TCT GGT AAA ACT CTG ACC ATC CAA GTC AAA       240
Ser Ser Glu Val Leu Gly Ser Gly Lys Thr Leu Thr Ile Gln Val Lys
65                  70                  75                  80

GAA TTT GGA GAT GCT GGC CAG TAT ACC TGC CAT AAA GGA GGC AAG GTT       288
Glu Phe Gly Asp Ala Gly Gln Tyr Thr Cys His Lys Gly Gly Lys Val
                85                  90                  95

CTG AGC CGC TCA CTC CTG TTG ATT CAC AAA AAA GAA GAT GGA ATT TGG       336
Leu Ser Arg Ser Leu Leu Leu Ile His Lys Lys Glu Asp Gly Ile Trp
            100                 105                 110

TCC ACT GAT ATC TTA AAG GAA CAG AAA GAA TCC AAA AAT AAG ATC TTT       384
Ser Thr Asp Ile Leu Lys Glu Gln Lys Glu Ser Lys Asn Lys Ile Phe
        115                 120                 125

CTG AAA TGT GAG GCA AAG AAT TAT TCT GGA CGT TTC ACA TGC TGG TGG       432
Leu Lys Cys Glu Ala Lys Asn Tyr Ser Gly Arg Phe Thr Cys Trp Trp
    130                 135                 140

CTG AGC GCA ATC AGT ACT GAT TTG AAA TTC AGT GTC AAA AGT AGC AGA       480
Leu Ser Ala Ile Ser Thr Asp Leu Lys Phe Ser Val Lys Ser Ser Arg
145                 150                 155                 160

GGC TTC TCT GAC CCC CAA GGG GTG ACA TGT GGA GCA GTG ACA CTT TCA       528
Gly Phe Ser Asp Pro Gln Gly Val Thr Cys Gly Ala Val Thr Leu Ser
                165                 170                 175

GCA GAG AGG GTC AGA GTG GAC AAC AGG GAT TAT AAG AAG TAC ACA GTG       576
Ala Glu Arg Val Arg Val Asp Asn Arg Asp Tyr Lys Lys Tyr Thr Val
            180                 185                 190

GAG TGT CAG GAG GGC AGT GCC TGC CCC TCT GCC GAG GAG AGC CTA CCC       624
Glu Cys Gln Glu Gly Ser Ala Cys Pro Ser Ala Glu Glu Ser Leu Pro
        195                 200                 205
```

-continued

```
ATC GAG GTC GTG GTG GAT GCT ATT CAC AAG CTC AAG TAT GAA AAC TAC         672
Ile Glu Val Val Val Asp Ala Ile His Lys Leu Lys Tyr Glu Asn Tyr
    210                 215                 220

ACC AGC AGC TTC TTC ATC AGA GAC ATC ATC AAA CCA GAC CCA CCC ACA         720
Thr Ser Ser Phe Phe Ile Arg Asp Ile Ile Lys Pro Asp Pro Pro Thr
225                 230                 235                 240

AAC CTG CAG CTG AAG CCA TTG GAA AAT TCT CGG CAC GTG GAG GTC AGC         768
Asn Leu Gln Leu Lys Pro Leu Glu Asn Ser Arg His Val Glu Val Ser
                245                 250                 255

TGG GAA TAC CCC GAC ACC TGG AGC ACC CCA CAT TCC TAC TTC TCC CTG         816
Trp Glu Tyr Pro Asp Thr Trp Ser Thr Pro His Ser Tyr Phe Ser Leu
            260                 265                 270

ACA TTT TGC ATA CAG GCC CAG GGC AAG AAC AAT AGA GAA AAG AAA GAT         864
Thr Phe Cys Ile Gln Ala Gln Gly Lys Asn Asn Arg Glu Lys Lys Asp
        275                 280                 285

AGA CTC TGC GTG GAC AAG ACC TCA GCC AAG GTC GTG TGC CAC AAG GAT         912
Arg Leu Cys Val Asp Lys Thr Ser Ala Lys Val Val Cys His Lys Asp
    290                 295                 300

GCC AAG ATC CGC GTG CAA GCC CGA GAC CGC TAC TAT AGT TCA TCC TGG         960
Ala Lys Ile Arg Val Gln Ala Arg Asp Arg Tyr Tyr Ser Ser Ser Trp
305                 310                 315                 320

AGC GAC TGG GCA TCT GTG CCC TGC AGT TAG                                 990
Ser Asp Trp Ala Ser Val Pro Cys Ser ***
                325                 330
```

(2) INFORMATION FOR SEQ ID NO: 2:

(i) SEQUENCE CHARACTERISTICS:
        (A) LENGTH: 669 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: Canis familiaris (ix) FEATURE:
        (A) NAME/KEY: Canine IL12
        (B) LOCATION: 1 to 666
        (C) IDENTIFICATION METHOD: Similarity (xi) SEQUENCE DESCRIPTION: SEQ ID NO: 2:

```
ATG TGT CCA GCG CGC AGC CTC CTC CTT GTC GCT ACC CTG GTC CTG CTA         48
Met Cys Pro Ala Arg Ser Leu Leu Leu Val Ala Thr Leu Val Leu Leu
1               5                   10                  15

AGC CAC CTG GAC CAC CTT ACT TGG GCC AGG AGC CTC CCC ACA GCC TCA         96
Ser His Leu Asp His Leu Thr Trp Ala Arg Ser Leu Pro Thr Ala Ser
                20                  25                  30

CCA AGC CCA GGA ATA TTC CAG TGC CTC AAC CAC TCC CAA AAC CTG CTG        144
Pro Ser Pro Gly Ile Phe Gln Cys Leu Asn His Ser Gln Asn Leu Leu
            35                  40                  45

AGA GCC GTC AGC AAC ACG CTT CAG AAG GCC AGA CAA ACT CTA GAA TTA        192
Arg Ala Val Ser Asn Thr Leu Gln Lys Ala Arg Gln Thr Leu Glu Leu
        50                  55                  60

TAT TCC TGC ACT TCC GAA GAG ATT GAT CAT GAA GAT ATC ACA AAG GAT        240
Tyr Ser Cys Thr Ser Glu Glu Ile Asp His Glu Asp Ile Thr Lys Asp
65                  70                  75                  80

AAA ACC AGC ACA GTG GAG GCC TGC TTA CCA CTG GAA TTA ACC ATG AAT        288
Lys Thr Ser Thr Val Glu Ala Cys Leu Pro Leu Glu Leu Thr Met Asn
                85                  90                  95

GAG AGT TGC CTG GCT TCC AGA GAG ATC TCT TTG ATA ACT AAC GGG AGT        336
```

```
               Glu Ser Cys Leu Ala Ser Arg Glu Ile Ser Leu Ile Thr Asn Gly Ser
                           100                 105                 110

TGC CTG GCC TCT GGA AAG GCC TCT TTT ATG ACG GTC CTG TGC CTT AGC        384
Cys Leu Ala Ser Gly Lys Ala Ser Phe Met Thr Val Leu Cys Leu Ser
        115                 120                 125

AGC ATC TAT GAG GAC TTG AAG ATG TAC CAG ATG GAA TTC AAG GCC ATG        432
Ser Ile Tyr Glu Asp Leu Lys Met Tyr Gln Met Glu Phe Lys Ala Met
130                 135                 140

AAC GCA AAG CTT TTA ATG GAT CCC AAG AGG CAG ATC TTT CTG GAT CAA        480
Asn Ala Lys Leu Leu Met Asp Pro Lys Arg Gln Ile Phe Leu Asp Gln
145                 150                 155                 160

AAC ATG CTG ACG GCT ATC GAT GAG CTG TTA CAG GCC CTG AAT TTC AAC        528
Asn Met Leu Thr Ala Ile Asp Glu Leu Leu Gln Ala Leu Asn Phe Asn
                165                 170                 175

AGT GTG ACT GTG CCA CAG AAA TCC TCC CTT GAA GAG CCG GAT TTT TAT        576
Ser Val Thr Val Pro Gln Lys Ser Ser Leu Glu Glu Pro Asp Phe Tyr
            180                 185                 190

AAA ACT AAA ATC AAG CTC TGC ATA CTT CTT CAT GCT TTC AGA ATT CGT        624
Lys Thr Lys Ile Lys Leu Cys Ile Leu Leu His Ala Phe Arg Ile Arg
                195                 200                 205

GCG GTG ACC ATC GAC AGA ATG ATG AGC TAT CTG AGT TCT TCC TAG            669
Ala Val Thr Ile Asp Arg Met Met Ser Tyr Leu Ser Ser Ser ***
210                 215                 220

(2) INFORMATION FOR SEQ ID NO: 3:

(i) SEQUENCE CHARACTERISTICS:
        (A) LENGTH: 33 bases
        (B) TYPE: nucleic acid
        (C) STRANDEDNESS: single
        (D) TOPOLOGY: linear (ii) MOLECULE TYPE: other nucleic acid; synthetic DNA (xi) SEQUENCE DESCRIPTION:  SEQ ID NO:3:

ATGTGTCACC AGCAGTTGGT CATCTCTTGG TTT                                   33

(2) INFORMATION FOR SEQ ID NO: 4:

(i) SEQUENCE CHARACTERISTICS:
        (A) LENGTH: 24 bases
        (B) TYPE: nucleic acid
        (C) STRANDEDNESS: single
        (D) TOPOLOGY: linear (ii) MOLECULE TYPE: other DNA; synthetic DNA (xi) SEQUENCE DESCRIPTION: SEQ ID NO: 4:

CTAACTGCAG GGCACAGATG CCCA                                             24

(2) INFORMATION FOR SEQ ID NO: 5:

(i) SEQUENCE CHARACTERISTICS:
        (A) LENGTH: 42 bases
        (B) TYPE: nucleic acid
        (C) STRANDEDNESS: single
        (D) TOPOLOGY: linear (ii) MOLECULE TYPE: other DNA; synthetic DNA (xi) SEQUENCE DESCRIPTION: SEQ ID NO: 5:

AGCATGTGTC AGCGCGCAG CCTCCTCCTT GTCGCTACCC TG                          42

(2) INFORMATION FOR SEQ ID NO: 6:
```

(i) SEQUENCE CHARACTERISTICS:
            (A) LENGTH: 39 bases
            (B) TYPE: nucleic acid
            (C) STRANDEDNESS: single
            (D) TOPOLOGY: linear (ii) MOLECULE TYPE: other DNA; synthetic DNA (xi) SEQUENCE DESCRIPTION: SEQ ID NO: 6:

CTAGGAAGAA CTCAGATAGC TCATCATTCT GTCGATGGT                                   39

(2) INFORMATION FOR SEQ ID NO: 7:

(i) SEQUENCE CHARACTERISTICS:
            (A) LENGTH: 39 bases
            (B) TYPE: nucleic acid
            (C) STRANDEDNESS: single
            (D) TOPOLOGY: linear (ii) MOLECULE TYPE: other DNA; synthetic DNA (xi) SEQUENCE DESCRIPTION: SEQ ID NO: 7:

GGGGAATTCA TGTGTCACCA GCAGTTGGTC ATCTCTTGG                                   39

(2) INFORMATION FOR SEQ ID NO: 8:

(i) SEQUENCE CHARACTERISTICS:
            (A) LENGTH: 39 bases
            (B) TYPE: nucleic acid
            (C) STRANDEDNESS: single
            (D) TOPOLOGY: linear (ii) MOLECULE TYPE: other DNA; synthetic DNA (xi) SEQUENCE DESCRIPTION: SEQ ID NO: 8:

CCCGAATTCC TAACTGCAGG GCACAGATGC CCAGTCGCT                                   39

(2) INFORMATION FOR SEQ ID NO: 9:

(i) SEQUENCE CHARACTERISTICS:
            (A) LENGTH: 39 bases
            (B) TYPE: nucleic acid
            (C) STRANDEDNESS: single
            (D) TOPOLOGY: linear (ii) MOLECULE TYPE: other DNA; synthetic DNA (xi) SEQUENCE DESCRIPTION: SEQ ID NO: 9:

GGGCTGCAGA TGTGTCCAGC GCGCAGCCTC CTCCTTGTC                                   39

(2) INFORMATION FOR SEQ ID NO: 10:

(i) SEQUENCE CHARACTERISTICS:
            (A) LENGTH: 39 bases
            (B) TYPE: nucleic acid
            (C) STRANDEDNESS: single
            (D) TOPOLOGY: linear (ii) MOLECULE TYPE: other DNA; synthetic DNA (xi) SEQUENCE DESCRIPTION: SEQ ID NO: 10:

GGGCTGCAGC TAGGAAGAAC TCAGATAGCT CATCATTCT                                   39

(2) INFORMATION FOR SEQ ID NO: 11:

(i) SEQUENCE CHARACTERISTICS:
            (A) LENGTH: 990 base pairs
            (B) TYPE: nucleic acid
            (C) STRANDEDNESS: double
            (D) TOPOLOGY: linear (ii) MOLECULE TYPE: cDNA to mRNA (vi) ORIGINAL SOURCE:
    (A) ORGANISM: Canis familiaris (ix) FEATURE:
    (A) NAME/KEY: Canine IL12
    (B) LOCATION: 1 to 987
    (C) IDENTIFICATION METHOD: Similarity (xi) SEQUENCE DESCRIPTION: SEQ ID NO: 11:

```
ATG CAT CCT CAG CAG TTG GTC ATC TCC TGG TTT TCC CTC GTT TTG CTG        48
Met His Pro Gln Gln Leu Val Ile Ser Trp Phe Ser Leu Val Leu Leu
 1               5                  10                  15

GCG TCT CCC CTC ATG GCC ATA TGG GAA CTG GAG AAA GAT GTT TAT GTT        96
Ala Ser Pro Leu Met Ala Ile Trp Glu Leu Glu Lys Asp Val Tyr Val
                20                  25                  30

GTA GAG TTG GAC TGG CAC CCT GAT GCC CCC GGA GAA ATG GTG GTC CTC       144
Val Glu Leu Asp Trp His Pro Asp Ala Pro Gly Glu Met Val Val Leu
            35                  40                  45

ACC TGC CAT ACC CCT GAA GAA GAT GAC ATC ACT TGG ACC TCA GCG CAG       192
Thr Cys His Thr Pro Glu Glu Asp Asp Ile Thr Trp Thr Ser Ala Gln
        50                  55                  60

AGC AGT GAA GTC CTA GGT TCT GGT AAA ACT CTG ACC ATC CAA GTC AAA       240
Ser Ser Glu Val Leu Gly Ser Gly Lys Thr Leu Thr Ile Gln Val Lys
    65                  70                  75                  80

GAA TTT GGA GAT GCT GGC CAG TAT ACC TGC CAT AAA GGA GGC AAG GTT       288
Glu Phe Gly Asp Ala Gly Gln Tyr Thr Cys His Lys Gly Gly Lys Val
                85                  90                  95

CTG AGC CGC TCA CTC CTG TTG ATT CAC AAA AAA GAA GAT GGA ATT TGG       336
Leu Ser Arg Ser Leu Leu Leu Ile His Lys Lys Glu Asp Gly Ile Trp
                100                 105                 110

TCC ACT GAT ATC TTA AAG GAA CAG AAA GAA TCC AAA AAT AAG ATC TTT       384
Ser Thr Asp Ile Leu Lys Glu Gln Lys Glu Ser Lys Asn Lys Ile Phe
            115                 120                 125

CTG AAA TGT GAG GCA AAG AAT TAT TCT GGA CGT TTC ACA TGC TGG TGG       432
Leu Lys Cys Glu Ala Lys Asn Tyr Ser Gly Arg Phe Thr Cys Trp Trp
        130                 135                 140

CTG ACG GCA ATC AGT ACT GAT TTG AAA TTC AGT GTC AAA AGT AGC AGA       480
Leu Thr Ala Ile Ser Thr Asp Leu Lys Phe Ser Val Lys Ser Ser Arg
145                 150                 155                 160

GGC TTC TCT GAC CCC CAA GGG GTG ACA TGT GGA GCA GTG ACA CTT TCA       528
Gly Phe Ser Asp Pro Gln Gly Val Thr Cys Gly Ala Val Thr Leu Ser
                165                 170                 175

GCA GAG AGG GTC AGA GTG GAC AAC AGG GAT TAT AAG AAG TAC ACA GTG       576
Ala Glu Arg Val Arg Val Asp Asn Arg Asp Tyr Lys Lys Tyr Thr Val
                180                 185                 190

GAG TGT CAG GAG GGC AGT GCC TGC CCC TCT GCC GAG GAG AGC CTA CCC       624
Glu Cys Gln Glu Gly Ser Ala Cys Pro Ser Ala Glu Glu Ser Leu Pro
            195                 200                 205

ATC GAG GTC GTG GTG GAT GCT ATT CAC AAG CTC AAG TAT GAA AAC TAC       672
Ile Glu Val Val Val Asp Ala Ile His Lys Leu Lys Tyr Glu Asn Tyr
        210                 215                 220

ACC AGC AGC TTC TTC ATC AGA GAC ATC ATC AAA CCA GAC CCA CCC ACA       720
Thr Ser Ser Phe Phe Ile Arg Asp Ile Ile Lys Pro Asp Pro Pro Thr
225                 230                 235                 240

AAC CTG CAG CTG AAG CCA TTG AAA AAT TCT CGG CAC GTG GAG GTC AGC       768
Asn Leu Gln Leu Lys Pro Leu Lys Asn Ser Arg His Val Glu Val Ser
                245                 250                 255

TGG GAA TAC CCC GAC ACC TGG AGC ACC CCA CAT TCC TAC TTC TCC CTG       816
Trp Glu Tyr Pro Asp Thr Trp Ser Thr Pro His Ser Tyr Phe Ser Leu
```

```
                260                 265                 270
ACA TTT TGC ATA CAG GCC CAG GGC AAG AAC AAT AGA GAA AAG AAA GAT      864
Thr Phe Cys Ile Gln Ala Gln Gly Lys Asn Asn Arg Glu Lys Lys Asp
        275                 280                 285

AGA CTC TGC GTG GAC AAG ACC TCA GCC AAG GTC GTG TGC CAC AAG GAT      912
Arg Leu Cys Val Asp Lys Thr Ser Ala Lys Val Val Cys His Lys Asp
    290                 295                 300

GCC AAG ATC CGC GTG CAA GCC CGA GAC CGC TAC TAT AGT TCA TCC TGG      960
Ala Lys Ile Arg Val Gln Ala Arg Asp Arg Tyr Tyr Ser Ser Ser Trp
305                 310                 315                 320

AGC GAC TGG GCA TCT GTG TCC TGC AGT TAG                              990
Ser Asp Trp Ala Ser Val Ser Cys Ser ***
                325                 330

(2) INFORMATION FOR SEQ ID NO: 12:

(i) SEQUENCE CHARACTERISTICS:
        (A) LENGTH: 669 base pairs
        (B) TYPE: nucleic acid
        (C) STRANDEDNESS: double
        (D) TOPOLOGY: linear (ii) MOLECULE TYPE: cDNA to mRNA (vi) ORIGINAL SOURCE:
        (A) ORGANISM: Canis familiaris (ix) FEATURE:
        (A) NAME/KEY: Canine IL12
        (B) LOCATION: 1 to 666
        (C) IDENTIFICATION METHOD: Similarity (xi) SEQUENCE DESCRIPTION: SEQ ID NO: 12:

ATG TGC CCG CCG CGC GGC CTC CTC CTT GTG ACC ATC CTG GTC CTG CTA       48
Met Cys Pro Pro Arg Gly Leu Leu Leu Val Thr Ile Leu Val Leu Leu
1                   5                   10                  15

AGC CAC CTG GAC CAC CTT ACT TGG GCC AGG AGC CTC CCC ACA GCC TCA       96
Ser His Leu Asp His Leu Thr Trp Ala Arg Ser Leu Pro Thr Ala Ser
                20                  25                  30

CCA AGC CCA GGA ATA TTC CAG TGC CTC AAC CAC TCC CAA AAC CTG CTG      144
Pro Ser Pro Gly Ile Phe Gln Cys Leu Asn His Ser Gln Asn Leu Leu
        35                  40                  45

AGA GCC GTC AGC AAC ACG CTT CAG AAG GCC AGA CAA ACT CTA GAA TTA      192
Arg Ala Val Ser Asn Thr Leu Gln Lys Ala Arg Gln Thr Leu Glu Leu
    50                  55                  60

TAT TCC TGC ACT TCC GAA GAG ATT GAT CAT GAA GAT ATC ACA AAG GAT      240
Tyr Ser Cys Thr Ser Glu Glu Ile Asp His Glu Asp Ile Thr Lys Asp
65                  70                  75                  80

AAA ACC AGC ACA GTG GAG GCC TGC TTA CCA CTG GAA TTA ACC ATG AAT      288
Lys Thr Ser Thr Val Glu Ala Cys Leu Pro Leu Glu Leu Thr Met Asn
                85                  90                  95

GAG AGT TGC CTG GCT TCC AGA GAG ATC TCT TTG ATA ACT AAC GGG AGT      336
Glu Ser Cys Leu Ala Ser Arg Glu Ile Ser Leu Ile Thr Asn Gly Ser
                100                 105                 110

TGC CTG GCC TCT GGA AAG GCC TCT TTT ATG ACG GTC CTG TGC CTT AGC      384
Cys Leu Ala Ser Gly Lys Ala Ser Phe Met Thr Val Leu Cys Leu Ser
        115                 120                 125

AGC ATC TAT GAG GAC TTG AAG ATG TAC CAG ATG GAA TTC AAG GCC ATG      432
Ser Ile Tyr Glu Asp Leu Lys Met Tyr Gln Met Glu Phe Lys Ala Met
    130                 135                 140

AAC GCA AAG CTT TTA ATG GAT CCC AAG AGG CAG ATC TTT CTG GAT CAA      480
Asn Ala Lys Leu Leu Met Asp Pro Lys Arg Gln Ile Phe Leu Asp Gln
145                 150                 155                 160
```

```
AAC ATG CTG ACA GCT ATC GAT GAG CTG TTA CAG GCC CTG AAT TTC AAC       528
Asn Met Leu Thr Ala Ile Asp Glu Leu Leu Gln Ala Leu Asn Phe Asn
            165                 170                 175

AGT GTG ACT GTG CCA CAG AAA TCC TCC CTT GAA GAG CCG GAT TTT TAT       576
Ser Val Thr Val Pro Gln Lys Ser Ser Leu Glu Glu Pro Asp Phe Tyr
            180                 185                 190

AAA ACT AAA ATC AAG CTC TGC ATA CTT CTT CAT GCT TTC AGA ATT CGT       624
Lys Thr Lys Ile Lys Leu Cys Ile Leu Leu His Ala Phe Arg Ile Arg
            195                 200                 205

GCG GTG ACC ATC GAT AGA ATG ATG AGT TAT CTG AAT TCT TCC TAA           669
Ala Val Thr Ile Asp Arg Met Met Ser Tyr Leu Asn Ser Ser ***
            210                 215                 220
```

(2) INFORMATION FOR SEQ ID NO: 13:

(i) SEQUENCE CHARACTERISTICS:
        (A) LENGTH: 39 bases
        (B) TYPE: nucleic acid
        (C) STRANDEDNESS: single
        (D) TOPOLOGY: linear (ii) MOLECULE TYPE: other DNA; synthetic DNA (xi) SEQUENCE DESCRIPTION: SEQ ID NO: 13:

GGGGAATTCA TGCATCCTCA GCAGTTGGTC ATCTCCTGG                             39

(2) INFORMATION FOR SEQ ID NO: 14:

(i) SEQUENCE CHARACTERISTICS:
        (A) LENGTH: 39 bases
        (B) TYPE: nucleic acid
        (C) STRANDEDNESS: single
        (D) TOPOLOGY: linear (ii) MOLECULE TYPE: other DNA; synthetic DNA (xi) SEQUENCE DESCRIPTION: SEQ ID NO: 14:

CCCGAATTCC TAACTGCAGG ACACAGATGC CCAGTCGCT                             39

(2) INFORMATION FOR SEQ ID NO: 15:

(i) SEQUENCE CHARACTERISTICS:
        (A) LENGTH: 39 bases
        (B) TYPE: nucleic acid
        (C) STRANDEDNESS: single
        (D) TOPOLOGY: linear (ii) MOLECULE TYPE: other DNA; synthetic DNA (xi) SEQUENCE DESCRIPTION: SEQ ID NO: 15:

GGGCTGCAGA TGTGCCCGCC GCGCGGCCTC CTCCTTGTG                             39

(2) INFORMATION FOR SEQ ID NO: 16:

(i) SEQUENCE CHARACTERISTICS:
        (A) LENGTH: 39 bases
        (B) TYPE: nucleic acid
        (C) STRANDEDNESS: single
        (D) TOPOLOGY: linear (ii) MOLECULE TYPE: other DNA; synthetic DNA (xi) SEQUENCE DESCRIPTION: SEQ ID NO: 16:

GGGCTGCAGT TAGGAAGAAT TCAGATAACT CATCATTCT                             39